United States Patent [19]
Uno et al.

[11] 3,992,391
[45] *Nov. 16, 1976

[54] 1,3-DISUBSTITUTED THIOUREA COMPOUNDS AND PREPARATION THEREOF

[75] Inventors: Hitoshi Uno, Takatsuki; Junji Nakano, Osaka; Toshiaki Kadokawa, Hirakata, all of Japan

[73] Assignee: Daenippon Pharmaceutical Co., Japan

[ * ] Notice: The portion of the term of this patent subsequent to Mar. 16, 1992, has been disclaimed.

[22] Filed: Aug. 16, 1972

[21] Appl. No.: 280,953

[52] U.S. Cl. .................... 260/294.8 H; 424/248; 424/250; 424/263; 260/240 G; 260/247.1 R; 260/268 H
[51] Int. Cl.² ...................................... C07D 213/74
[58] Field of Search .................. 260/240 G, 294.8 H

[56] References Cited
UNITED STATES PATENTS
2,657,234  10/1953  Klarer et al. .................. 260/294.8 H
3,412,098  11/1968  Winkelmann et al. ........ 260/294.8 H FOREIGN PATENTS OR APPLICATIONS
216,695  7/1968  U.S.S.R. ...................... 260/294.8 H OTHER PUBLICATIONS
C.A. 75:20217c, (1971), Minami, et al.

*Primary Examiner*—John D. Randolph
*Attorney, Agent, or Firm*—Bierman & Bierman

[57] ABSTRACT

1,3-Disubstituted thiourea compounds represented by the following formula:

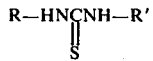

and their pharmaceutically acceptable acid addition salts which are useful especially for prevention and treatment of hypoxemia and further various diseases caused by hypoxia in local tissues, and process for the preparation of the present compounds set forth above and pharmaceutical composition containing the present compounds as an essential active ingredient.

3 Claims, No Drawings

1,3-DISUBSTITUTED THIOUREA COMPOUNDS AND PREPARATION THEREOF

The present invention relates to novel 1,3-disubstituted thiourea compounds and their pharmaceutically acceptable acid addition salts and process for the preparation thereof and composition containing the 1,3-disubstituted thiourea compounds and their salts. More particularly, it relates to 1,3-disubstituted thiourea compounds represented by the following formula:

  [I]

wherein one of R and R' represents a pyridyl group and another one of them represents a pyridyl group, a lower alkyl group substituted with lower alkoxy, hydroxy, lower alkoxycarbonyl, carboxyl, aralkylthio, $N^3$-pyridylthioureidoalkyldithio or lower alkylamino, an amino group substituted or not with lower alkyl, aryl, aralkyl or acyl, a morpholino group, a piperazino group substituted or not with aralkyl or a lower alkylideneamino group substituted or not with pyridyl on the alkylidene group, and their pharmaceutically acceptable acid addition salts and process for the preparation thereof and composition containing the 1,3-disubstituted thiourea compounds or their pharmaceutically acceptable acid addition salts.

Suitable examples of the substituent defined by R or R' are a lower alkyl group substituted with hydroxyl group or carboxyl group, phenylamino group, N-benzyl-N-methylamino group, N'-benzylpiperazinyl group and 3'-pyridylmethylideneamino group.

Suitable examples of the present 1,3-disubstituted thiourea compounds are 1-(2'-pyridyl)-3-(2'-hydroxyethyl)thiourea, 1-(3'-pyridyl)-3-(2'-hydroxyethyl)thiourea, 1-(3'-pyridyl)-3-(3'-hydroxypropyl)thiourea, 1-(3'-pyridyl)-3-(1',1'-dimethyl-2'-hydroxyethyl)thiourea, 1-(3'-pyridyl)-3-(2'-hydroxypropyl)thiourea, 1-(3'-pyridyl)-3-(3'-carboxypropyl)thiourea, 1-(3'-pyridyl)-3-phenylaminothiourea, 1-(3'-pyridyl)- 3-(N-benzyl-N-methylamino)thiourea, 1-(3'-pyridyl)-3-(N'-benzylpiperadinyl)thiourea, 1-(3'-pyridyl)-3-(2'-pyridylmethylideamino)thiourea, 1-(3'-pyridyl)-3-(3'-pyridylmethylideneamino)thiourea, 1-(4'-pyridyl)-3-(2'-hydroxyethyl)thiourea and 1-(4'-pyridyl)-3-(N-benzyl-N-methylamino)thiourea, and the pharmaceutically acceptable acid addition salt thereof.

The present 1,3-disubstituted thiourea compounds and their pharmaceutically acceptable acid addition salts can be prepared by reacting an amine of the following formula:

R—NH₂   [II]

wherein R is the same as defined above or its salt with an isothiocyanate of the following formula:
R'—NCS   [III]

wherein R' is the same as defined above or with a dithiocarbamate of the following formula:

R'—HNCSS—A   [III']

wherein R' is the same as defined above and A is a lower alkyl group.

The reaction of the amine [II] with the isothiocyanate [III] or the dithiocarbamate [III'] can be carried out at room temperature or under heating, e.g. at a reflux temperature of a solvent in an appropriate solvent.

As the solvent, there may be employed an inert one which does not inhibit the reaction. The suitable examples are ethyl ether, chloroform, acetone, acetonitrile, ethanol or water. Alternatively, the starting compounds may serve as the solvent depending on their properties.

When the amine [II] is used in a form of salt with an inorganic or organic acid (e.g. hydrochloric acid or sulfuric acid), the reaction is preferably carried out in the presence of a basic substance to neutralize the salt, such as an inorganic base (e.g. sodium hydroxide or sodium carbonate) or more preferably an organic base (e.g. trimethylamine or triethylamine).

Depending on the kinds of the starting compounds and the conditions of the reaction and the treatment after the reaction, the desired compounds [I] may be obtained in the free form or in a salt form. The salt can be converted into its free form by conventional methods such as the treatment with an alkaline substance (e.g. a hydroxide, carbonate or bicarbonate of an alkali metal or alkaline earth metal, for example sodium hydroxide, potassium hydroxide, sodium carbonate, potassium carbonate or sodium bicarbonate) or with an ion-exchange resin. On the other hand, the free 1,3-disubstituted thiourea compound can form its pharmaceutically acceptable acid addition salt by reacting with an inorganic or organic acid (e.g. hydrochloric acid, phosphoric acid, sulfuric acid, hydrobromic acid, hydroiodic acid, citric acid, lactic acid, maleic acid, malic acid, tartaric acid, acetic acid, benzoic acid or ascorbic acid). Further, the salt interchange can be effected between an acid addition salt of the compound [I] and an another acid.

The 1,3-disubstituted thiourea compounds [I] and their pharmaceutically acceptable acid addition salts of the present invention possess superior pharmacological activities, e.g. inhibitory action against various kinds of hypoxia such as tissue-toxic hypoxia, atmospheric hypoxia and hypotonic hypoxia. It has been known that hypoxia in tissue results in an increase of penetrability of electrolyte which causes of edema and finally failure of function of the tissue, and that the tolerance of tissue against hypoxia is worse especially in cerebral and heart. In facts, latent injuries of cerebrovascular diseases and myocardial infarction are caused or worsened by hypoxia in tissue. The present compounds function increasing the tolerance of tissue against hypoxia. Experimentally, the present compounds showed inhibitory action against decrease of glycogen, increase of lactate and lowering of $Na^+$, $K^+$ - adenosine triphosphatase (hereinafter, referred to as ATPase) activity which are observed in cerebral of rats having experimental cerebral edema, and maintained the cerebral water content. Further, the present compounds showed inhibitory action against decrease of glycogen and increases of pyruvate, lactate and non-esterified fatty acids which are observed in heart of rats having experimental heart-failure. Accordingly, the present compounds are useful as medicaments, especially for prevention and treatment of hypoxemia and further various diseases caused by hypoxia in local tissues, such as cerebrovascular diseases, myocardial infarction and kidney insufficiency.

The 1,3-disubstituted thioruca compounds [I] and their pharmaceutically acceptable acid addition salts can be administered orally or parenterally (e.g. intravenously) by conventional methods and with conventional pharmaceutical carriers in humans. They can be used in a form of tablets, capsules, powders or in a liquid form, such as solutions, emulsions, suspensions or syrups for oral administration, and in a form of solution in water, which is, if necessary, buffered or made isotonic, for parenteral administration.

The dosage per day of the present compounds for oral administration is within the range of 2 to 60 mg per kg of body weight, preferably within the range of 3 to 20 mg per kg of body weight, more particularly the range of 6 to 12 mg per kg of body weight. The dosage per day of the present compounds for intravenous injection is within the range of 0.2 to 20 mg per kg of body weight, preferably within the range of 0.5 to 15 mg per kg of body weight, more particularly the range of 1 to 4 mg per kg of body weight.

The preparation of the present 1,3-disubstituted thiourea compounds and their pharmaceutically acceptable acid addition salts is set out in the following Examples which are illustrative but not limiting.

EXAMPLE 1

Preparation of 1-(3'-pyridyl)-3-(3'-dimethylaminopropyl)thiourea:

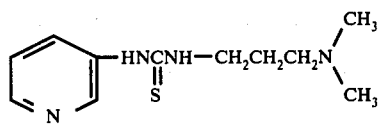

To a solution of 3-dimethylamino-n-propylamine (1.7 g) in ethyl ether (20 ml), a solution of 3-pyridylisothiocyanate (2.0 g) in ethyl ether (10 ml) is added while stirring whereby an exothermic reaction occurs. The precipitated white crystals are collected by filtration, washed with ethyl ether and dried. Recrystallization from ethyl acetate gives 1-(3'-pyridyl)-3-(3'-dimethylaminopropyl)thiourea (2.5 g). M.P. 103° to 107° C. Yield, 71 %.

Anal. Calcd. for $C_{11}H_{18}N_4S$: C, 55.43; H, 7.61; N, 23.51; S, 13.45. Found: C, 55.46; H, 7.72; N, 23.20; S, 13.37.

EXAMPLE 2

Preparation of 1-(3'-pyridyl)-3-(2'-benzylthioethyl)thiourea:

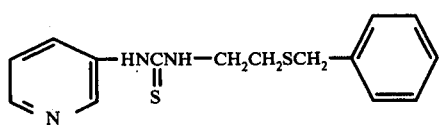

To a suspension of S-benzylcysteamine hydrochloride (2.1 g) in chloroform (20 ml), triethylamine (2 ml) is added, and the mixture is stirred to make a solution. A solution of 3-pyridylisothiocyanate (1.2 g) in chloroform (10 ml) is added thereto while stirring. The resultant mixture is reacted for 1 hour and then concentrated to remove the solvent. The residue is admixed with water and extracted with ethyl acetate. The ethyl acetate layer is dried over sodium sulfate and concentrated. The residual crystals are recrystallized from ethyl acetate to give 1-(3'-pyridyl)-3-(2'-benzylthioethyl)thiourea (1.7 g). M.P. 97° to 99° C. Yield, 64 %.

Anal. Calcd. for $C_{15}H_{17}N_3S_2$: C, 59.37; H, 5.65; N, 13.85; S, 21.13. Found: C, 59.38; H, 5.57; N, 13.55; S, 21.10.

EXAMPLE 3

Preparation of 1-(3'-pyridyl)-3-(3'-diethylaminopropyl)thiourea:

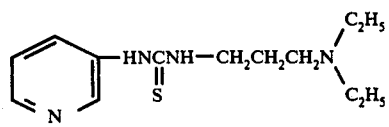

To a solution of S-methyl-3-pyridyldithiocarbamate (0.92 g) in ethanol (20 ml), 3-diethylaminopropylamine (1.5 g) is added, and the mixture is heated under reflux for 2 hours on a water bath. After cooling, the solvent is evaporated under reduced pressure. The residual crystals are recrystallized from ethyl acetate to give 1-(3'-pyridyl)-3-(3'-diethylaminopropyl)thiourea (1.2 g). M.P. 114° to 116° C. Yield, 90 %.

Anal. Calcd. for $C_{13}H_{22}N_4S$: C, 58.61; H, 8.32; N, 21.03; S, 12.04. Found: C, 58.65; H, 8.26; N, 20.74; S, 12.11.

EXAMPLE 4

Preparation of 1-(4'-pyridyl)-3-(2'-diethylaminoethyl)thiourea:

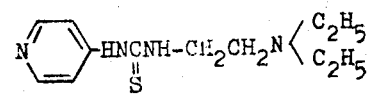

A mixture of S-methyl-4-pyridylaminodithiocarbamate (1.4 g), ethanol (30 ml) and 2-diethylaminoethylamine (1.7 g) is heated under reflux for 3 hours, and then the solvent is evaporated under reduced pressure. The residual crystals are washed with ethyl ether and recrystallized from ethyl acetate to give 1-(4'-pyridyl)-3-(2'-diethylaminoethyl)thiourea (1.4 g). M.P. 95° to 97° C. Yield, 73 %.

Anal. Calcd. for $C_{12}H_{20}N_4S$: C, 57.11; H, 7.99; N, 22.20; S, 12.70. Found: C, 57.42; H, 7.96; N, 22.23; S, 12.70.

EXAMPLE 5

Preparation of 1-(2'-pyridyl)-3-(2'-hydroxyethyl)thiourea hydrochloride:

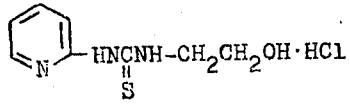

A mixture of S-methyl-2-pyridylaminodithiocarbamate (2 g), ethanol (13 ml) and 2-aminoethanol (1 g) is heated under reflux for 3 hours. After cooling, the solvent is evaporated under reduced pressure. To the residue, alcoholic hydrochloric acid is added, and the precipitated crystals are recrystallized from a water-ethanol mixture to give 1-(2'-pyridyl)-3-(2'-hydroxyethyl)thiourea hydrochloride (1.5 g). M.P. 171° to 173° C (decomp.) Yield, 59 %.

Anal. Calcd. for C₈H₁₁N₃SO.HCl: C, 41.11; H, 5.17; N, 17.98; S, 13.72; Cl, 15.17. Found: C, 41.41; H, 5.20; N, 18.13; S, 13.64; Cl, 14.92.

EXAMPLE 6

Preparation of 1-(3'-pyridyl)-3-(2'-ethoxycarbonylethyl)thiourea:

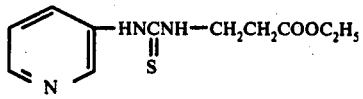

To a solution of 3-aminopyridine (1.4 g) in ethyl ether (50 ml), an etheral solution of ethyl 3-isothiocyanopropionate (2.6 g) is dropwise added while stirring under ice-cooling. The resultant mixture is allowed to stand at room temperature over night. Ethyl ether is evaporated under reduced pressure, and the residual crystals are recrystallized from ethyl acetate to give 1-(3'-pyridyl)-3-(2'-ethoxycarbonylethyl)thiourea (2.8 g). M.P. 92° to 94° C. Yield, 74 %.

Anal. Calcd. for C₁₁H₁₅N₃O₂S: C, 52.16; H, 5.97; N, 16.59; S, 12.66. Found: C, 52.11; H, 5.94; N, 16.62; S, 12.50.

EXAMPLE 7

Preparation of 1-(3'-pyridyl)-3-(2'-hydroxyethyl)thiourea hydrochloride:

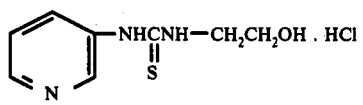

A mixture of S-methyl-3'-pyridyldithiocarbamate (8 g), 2-aminoethanol (3.5 g) and ethanol (100 ml) is heated under reflux for 2 hours. After evaporating ethanol, the precipitated crystals are washed with ethyl ether and then dissolved in methanol. To the solution is added methanolic hydrochloric acid, and the precipitated crystals are collected by filtration and recrystallized from diluted ethanol to give 1-(3'-pyridyl)-3-(2'-hydroxyethyl)thiourea hydrochloride (8.5 g). M.P. 176° to 178° C (decomp.). Yield, 83.7 %.

Anal. Calcd. for C₈H₁₁N₃OS.HCl: C, 41.11; H, 5.17; N, 17.98; S, 13.72; Cl, 15.17. Found: C, 41.39; H, 5.14; N, 17.80; S, 13.21; Cl, 15.30.

EXAMPLE 8

Preparation of 1-(3'-pyridyl)-3-(2'-hydroxyethyl)thiourea hydrochloride:

To a solution of 2-aminoethanol (0.7 g) in chloroform (30 ml) is added 3-pyridylisothiocyanate (1.4 g) while stirring under cooling. The resultant mixture is stirred at room temperature for one hour. After evaporating chloroform, the precipitated crystals are washed with ethyl ether and then dissolved in methanol. To the solution is added methanolic hydrochloric acid, and the precipitated crystals are collected by filtration and recrystallized from diluted ethanol to give 1-(3'-pyridyl)-3-(2'-hydroxyethyl)thiourea hydrochloride (1.9 g). M.P. 176° to 178° C (decomp.). Yield, 80 %.

EXAMPLES 9 TO 35

In the same manner as described in Examples 1 to 8, various thiourea compounds are prepared, which are shown in Table I.

Table I

| Ex. No. | Structural formula | M.P. (°C.) | Molecular formula | Elementary analysis | C | H | N | S | Cl |
|---|---|---|---|---|---|---|---|---|---|
| 9 | 3-pyridyl-HNCNH—CH₂CH₂OH (C=S) | 121–122 | C₈H₁₁N₃OS | Calcd. Found | 48.71 49.10 | 5.62 5.68 | 21.30 21.16 | 16.25 15.92 | |
| 10 | 3-pyridyl-HNCNH—CH₂CH₂CH₂OH . HCl (C=S) | 165–166 | C₉H₁₃N₃OS . HCl | Calcd. Found | 43.63 43.40 | 5.70 5.59 | 16.96 16.78 | 12.94 12.77 | 14.31 14.46 |
| 11 | 3-pyridyl-HNCNH—C(CH₃)₂—CH₂OH . HCl (C=S) | 165–166 | C₁₀H₁₅N₃OS . HCl | Calcd. Found | 45.88 45.64 | 6.16 6.14 | 16.05 16.03 | 12.25 12.03 | 13.54 14.38 |
| 12 | 3-pyridyl-HNCNH—CH₂CHCH₃ . HCl, OH (C=S) | 195–197 | C₉H₁₃N₃OS . HCl | Calcd. Found | 43.63 43.80 | 5.70 5.80 | 16.96 16.76 | 12.94 12.79 | 14.31 14.49 |
| 13 | 3-pyridyl-HNCNH—C(CH₂OH)₃ (C=S) | 157–159 | C₁₀H₁₅N₃O₃S | Calcd. Found | 46.68 46.77 | 5.88 5.94 | 16.33 16.10 | 12.46 12.56 | |
| 14 | 3-pyridyl-HNCNH—CH₂CH₂CH₂OCH₃ . HCl (C=S) | 125–127 | C₁₀H₁₅N₃OS . HCl | Calcd. Found | 45.88 46.47 | 6.16 6.12 | 16.05 15.91 | 12.25 12.50 | 13.54 13.59 |
| 15 | 3-pyridyl-HNCNH—CH₂CH₂CH₂COOH (C=S) | 177–178 | C₁₀H₁₃N₃O₂S | Calcd. Found | 50.19 50.11 | 5.48 5.51 | 17.56 17.21 | 13.40 13.36 | |

Table I-continued

| Ex. No. | Structural formula | M.P. (°C.) | Molecular formula | Elementary analysis |  |  |  |  |
|---|---|---|---|---|---|---|---|---|
|  |  |  |  | C | H | N | S | Cl |
| 16 | (pyridin-3-yl-HNCNH-CH₂CH₂S—)₂ · 2HCl · H₂O, C=S | 121–124 | C₁₆H₂₀N₆S₄ · 2HCl · H₂O | Calcd. 37.27<br>Found 37.44 | 4.69<br>4.88 | 16.30<br>16.01 | 24.88<br>24.34 | 13.75<br>13.59 |
| 17 | pyridin-3-yl-HNCNH—CH₂CH₂N(CH₃)₂, C=S | 111–114 | C₁₀H₁₆N₄S | Calcd. 53.54<br>Found 53.84 | 7.19<br>7.40 | 24.98<br>24.86 | 14.29<br>14.08 |  |
| 18 | pyridin-3-yl-HNCNH—CH₂CH₂N(C₂H₅)₂, C=S | 100–101 | C₁₂H₂₀N₄S | Calcd. 57.11<br>Found 56.95 | 7.99<br>7.96 | 22.20<br>22.10 | 12.70<br>12.62 |  |
| 19 | pyridin-3-yl-HNCNH—NH₂, C=S | 170 | C₆H₈N₄S | Calcd. 42.84<br>Found 42.63 | 4.76<br>4.57 | 33.31<br>32.89 | 19.06<br>18.51 |  |
| 20 | pyridin-3-yl-HNCNH—NH—phenyl, C=S | 116–117.5 | C₁₂H₁₂N₄S | Calcd. 58.99<br>Found 58.86 | 4.95<br>5.09 | 22.93<br>22.82 | 13.12<br>12.93 |  |
| 21 | pyridin-3-yl-HNCNH—NHCOCH(phenyl)₂ · ½C₂H₅OH, C=S | 165–167 | C₂₀H₁₉N₄OS · ½C₂H₅OH | Calcd. 65.69<br>Found 65.20 | 5.34<br>5.62 | 14.83<br>14.24 | 8.49<br>8.13 |  |
| 22 | pyridin-3-yl-HNCNH—N(CH₂-phenyl)(CH₃), C=S | 134.5–135 | C₁₄H₁₆N₄S | Calcd. 61.74<br>Found 61.86 | 5.92<br>6.04 | 20.57<br>20.27 | 11.77<br>11.59 |  |
| 23 | pyridin-3-yl-HNCNH—NHCOCH(phenyl)(C₂H₅), C=S | 160 | C₁₆H₁₈N₄OS | Calcd. 61.12<br>Found 61.12 | 5.77<br>5.80 | 17.82<br>17.65 | 10.20<br>10.33 |  |
| 24 | pyridin-3-yl-HNCNH—N(morpholino), C=S | 209–211 | C₁₀H₁₄N₄OS | Calcd. 50.40<br>Found 50.42 | 5.92<br>5.92 | 23.51<br>23.40 | 13.45<br>13.46 |  |
| 25 | pyridin-3-yl-HNCNH—N(piperazinyl)-N-CH₂-phenyl, C=S | 165 | C₁₇H₂₁N₅S | Calcd. 62.36<br>Found 62.06 | 6.46<br>6.57 | 21.39<br>21.20 | 9.79<br>9.75 |  |
| 26 | pyridin-3-yl-HNCNH—N=C(CH₃)₂, C=S | 169–170.5 | C₉H₁₂N₄S | Calcd. 51.90<br>Found 51.83 | 5.81<br>5.90 | 26.90<br>26.66 | 15.39<br>15.05 |  |
| 27 | pyridin-3-yl-HNCNH—N=CH-pyridin-2-yl, C=S | 198–200 | C₁₂H₁₁N₅S | Calcd. 56.01<br>Found 55.80 | 4.31<br>4.41 | 27.22<br>26.96 | 12.46<br>12.51 |  |

Table I-continued

| Ex. No. | Structural formula | M.P. (°C.) | Molecular formula | Elementary analysis |  |  |  |  |
|---|---|---|---|---|---|---|---|---|
|  |  |  |  |  | C | H | N | S | Cl |
| 28 | pyridine-HNCNH-N=CH-pyridine (C=S) | 202–203 | $C_{12}H_{11}N_5S$ | Calcd. Found | 56.01 56.27 | 4.31 4.44 | 27.22 27.06 | 12.46 12.30 |
| 29 | pyridine-HNCNH-CH$_2$CH$_2$OH (C=S) | 162–163 | $C_8H_{11}N_3OS$ | Calcd. Found | 48.71 49.08 | 5.62 5.81 | 21.30 21.32 | 16.25 16.03 |
| 30 | pyridine-HNCNH-CH$_2$CH$_2$CH$_2$N(CH$_3$)$_2$ (C=S) | 115–116 | $C_{11}H_{18}N_4S$ | Calcd. Found | 55.43 55.15 | 7.61 7.60 | 23.51 23.05 | 13.45 13.56 |
| 31 | pyridine-HNCNH-CH$_2$CH$_2$SCH$_2$-phenyl (C=S) | 140–141 | $C_{15}H_{17}N_3S_2$ | Calcd. Found | 59.37 59.38 | 5.65 5.65 | 13.85 13.64 | 21.13 21.16 |
| 32 | pyridine-HNCNH-N(CH$_3$)(CH$_2$-phenyl) (C=S) | 147–148 | $C_{14}H_{16}N_4S$ | Calcd. Found | 61.74 62.07 | 5.92 6.08 | 20.57 20.28 | 11.77 11.88 |
| 33 | pyridine-HNCNH-CH$_2$CH$_2$CH$_2$COOH · HCl (C=S) | 193–195 | $C_{10}H_{13}N_3O_2S$ · HCl | Calcd. Found | 43.56 43.65 | 5.12 5.12 | 15.24 15.02 | 11.63 12.33 | 12.86 12.80 |
| 34 | pyridine-HNCHN-CH$_2$CH$_2$SCH$_2$-phenyl (C=S) | 107 | $C_{15}H_{17}N_3S_2$ | Calcd. Found | 59.37 59.65 | 5.65 5.82 | 13.85 13.90 | 21.13 21.33 |
| 35 | pyridine-HNCNH-CH$_2$CH$_2$N(C$_2$H$_5$)$_2$ · 2HCl (C=S) | 181–183 | $C_{12}H_{20}N_4S$ · 2HCl | Calcd. Found | 44.31 44.22 | 6.82 6.91 | 17.22 17.52 | 9.86 9.95 | 21.80 21.90 |

1,3-Disubstituted thiourea compounds and their pharmaceutically acceptable acid addition salts prepared in accordance with the foregoing procedure were administered to laboratory test animals following established procedures and were found to exhibit unexpected and desirable pharmacological properties. The following Examples are representative of such determinations.

EXAMPLE 36 a. Effect on tissue-toxic hypoxia

To male mice (dd-strain) weighting 15 to 22g were administered orally the present compounds in the dosage of 100 mg/kg, and after one hour, KCN (10 mg/kg) was administered intraperitoneally. The time for death was measured. The increase percent of survival time to the average survival time (140 seconds) of the group, to which the present compounds were not administered, is shown in Table II as life-prolonging rate (1).

b. Effect on hyptonic hypoxia

To male mice (dd-strain) weighting 15 to 22 g were administered orally the present compounds in the dosage of 100 mg/kg, and after one hour, the mice were taken to a closed room, air in which was substituted with nitrogen gas containing 1.5 % oxygen by ventilating the nitrogen gas for 2 minutes. As sending a mixed gas into the room, the time for death was measured. The increase percent of survival time to the average survival time (8 minutes) of the group, to which the present compounds were not administered, is shown in Table II as life-prolonging rate (2).

Table II

| Test compounds | Life-prolonging rate |  |
|---|---|---|
|  | (1) | (2) |
| pyridine-HNCNH-CH$_2$CH$_2$CH$_2$N(CH$_3$)$_2$ (C=S) | 35 | 10 |

Table II-continued

| Test compounds | Life-prolonging rate (1) | (2) |
|---|---|---|
| 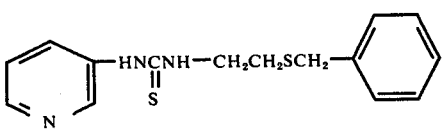 pyridyl-HNCNH-CH₂CH₂SCH₂-phenyl, C=S | 64 | 55 |
| 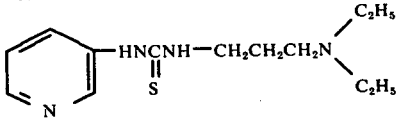 pyridyl-HNCNH-CH₂CH₂CH₂N(C₂H₅)₂, C=S | 28 | 11 |
| 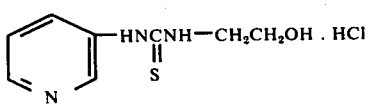 pyridyl-HNCNH-CH₂CH₂OH · HCl, C=S | 131 | 68 |
| 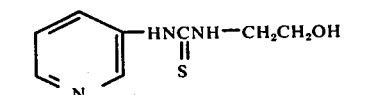 pyridyl-HNCNH-CH₂CH₂OH, C=S | 251 | 126 |
| 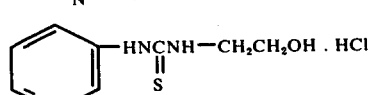 pyridyl-HNCNH-CH₂CH₂OH · HCl, C=S | 189 | 165 |
| 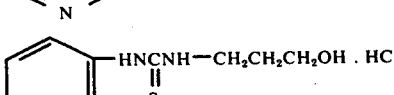 pyridyl-HNCNH-CH₂CH₂CH₂OH · HCl, C=S | 115 | 100 |
| 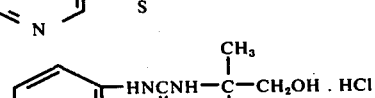 pyridyl-HNCNH-C(CH₃)₂-CH₂OH · HCl, C=S | 67 | 50 |
| 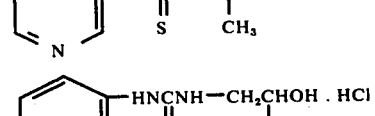 pyridyl-HNCNH-CH₂CHOH·CH₃ · HCl, C=S | 75 | 60 |
| 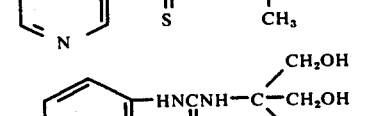 pyridyl-HNCNH-C(CH₂OH)₃, C=S | 61 | 59 |
| 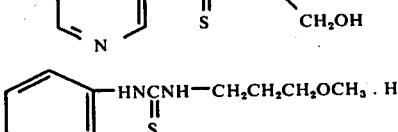 pyridyl-HNCNH-CH₂CH₂CH₂OCH₃ · HCl, C=S | 35 | 25 |
|  pyridyl-HNCNH-CH₂CH₂CH₂COOH, C=S | 127 | 78 |
| 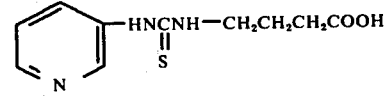 (pyridyl-HNCNH-CH₂CH₂S-)₂ · 2HCl · H₂O, C=S | 30 | 5 |
| 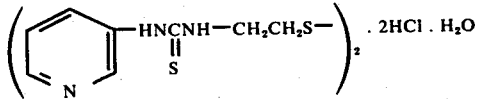 pyridyl-HNCNH-CH₂CH₂N(CH₃)₂, C=S | 61 | 46 |
| 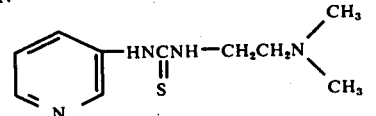 pyridyl-HNCNH-CH₂CH₂N(C₂H₅)₂, C=S | 89 | 40 |
| 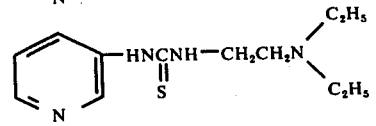 pyridyl-HNCNH-NHNH-phenyl, C=S | 125 | 108 |

Table II-continued

| Test compounds | Life-prolonging rate (1) | (2) |
|---|---|---|
| 3-pyridyl-HNCNH(S)-N(CH₂)(CH₂) (dimethylamino derivative) | 81 | 63 |
| 3-pyridyl-HNCNH(S)-N-piperazinyl-N-CH₂-phenyl | 124 | 80 |
| 3-pyridyl-HNCNH(S)-N=CH-2-pyridyl | 92 | 81 |
| 3-pyridyl-HNCNH(S)-N=CH-3-pyridyl | 135 | 114 |
| 4-pyridyl-HNCNH(S)-CH₂CH₂OH | 242 | 158 |
| 4-pyridyl-HNCNH(S)-CH₂CH₂CH₂N(CH₃)(CH₃) | 37 | 21 |
| 4-pyridyl-HNCNH(S)-N(CH₃)(CH₂-phenyl) | 156 | 58 |
| 2-pyridyl-HNCNH(S)-CH₂CH₂CH₂COOH · HCl | 72 | 53 |
| 2-pyridyl-HNCNH(S)-CH₂CH₂SCH₂-phenyl | 86 | 65 |
| 2-pyridyl-HNCNH(S)-CH₂CH₂N(C₂H₅)(C₂H₅) · 2HCl | 20 | 16 |

EXAMPLE 37

Prolonging effect of 1-(3′-pyridyl)-3-(2′-hydroxyethyl)thiourea hydrochloride by the lethal time induced with various hypoxic conditions Male mice (dd-strain) and rats (wister-strain) were taken to a closed room which was filled with a gas mixture consisting of 1.5 % oxygen and 98.5 % nitrogen, or was conditioned in reduced atmospheric pressure (145 mmHg). In the other hand, mice and rats were given sodium cyanide (10 mg/kg, i.p.). These animals died after a few minutes in such conditions. 1-(3′-Pyridyl)-3-(2′-hydroxyethyl)thiourea HCl was given 1 hour before these hypoxia tests.

When the animals were given 1-(3′-pyridyl)-3-(2′-hydroxyethyl)thiourea HCl in the dosages of 100, 300 mg/kg p.o., 100 mg/kg s.c., and 30 mg/kg i.v., they survived twice or more in comparison with the survival time of each control group, to which the test compound was not administered. These results are shown in Tables III and IV. In the Tables data mean the increase percent of the survival time to that of control.

Table III

| Test compound | Route | Dose (mg/kg) | Hypoxia test (mouse) Normal pressure* | Reduced pressure** | KCN*** |
|---|---|---|---|---|---|
| Control | — | — | 8.0 ± 0.89 (min) | 4.2 ± 2.10 (min) | 4.0 ± 0.92 (min) |

Table III-continued

| Test compound | Route | Dose (mg/kg) | Hypoxia test (mouse) | | |
|---|---|---|---|---|---|
| | | | Normal pressure* | Reduced pressure** | KCN*** |
| 1-(30'-Pyridyl)-3-(2'-hydroxyethyl)thiourea HCl | p.o. | 30 | 105 | 35 | 42 |
| | | 100 | 165 | 64 | 189 |
| | | 300 | 231 | 132 | 287 |
| | s.c. | 100 | 147 | 128 | 254 |
| | i.v. | 30 | 164 | 141 | 185 |

Note:
*1.5 % $O_2$ + 98.5 % $N_2$;
**145 mmHg (Ca. 5 % $O_2$);
***KCN 10 mg/kg, i.p.

Table IV

| Test compound | Route | Dose (mg/kg) | Hypoxia test (rat) | | |
|---|---|---|---|---|---|
| | | | Normal pressure* | Reduced pressure** | KCN*** |
| Control | — | — | 6.8 ± 1.47 (min) | 10.4 ± 1.05 (min) | 2.0 ± 0.11 (min) |
| 1-(3'-Pyridyl)-3-(2'-hydroxyethyl)thiourea HCl | p.o. | 30 | 36 | | 45 |
| | | 100 | 75 | | 116 |
| | | 300 | 153 | | 187 |
| | s.c. | 100 | 192 | 132 | 169 |
| | i.v. | 30 | 148 | 135 | 174 |

Note:
*1.5 % $O_2$ + 98.5 % $N_2$;
**145 mmHg (Ca. 5 % $O_2$);
***KCN 10 mg/kg, i.p.

EXAMPLE 38

Effects of 1-(3'-pyridyl)-3-(2'-hydroxyethyl)thiourea hydrochloride on the cerebral phosphorylase, $Na^+$, $K^+$ - ATPase and water changes induced with cold injury.

Cerebral edema was induced in rats by a freezing lesion (dry ice) made on the exposed dura of unilateral hemisphere. Edema was measured by the increase in water content of gray and white matter, the increase in phosphorylase activity and the decrease in $Na^+$, $K^+$ - ATPase activity of the injured brain. 1-(3'-Pyridyl)-3-(2'-hydroxyethyl)thiourea HCl was given 1 hour before and 24 hours after, and the animals were killed by decapitation 48 hours after the lesion treatment.

1-(3'-Pyridyl)-3-(2'-hydroxyethyl)thiourea HCl had protective effect to the increase in water content and phosphorylase activity and to the decrease in $Na^+$, $K^+$ - ATPase activity in the dosage of 300 mg/kg p.o. The results are shown in Table V.

EXAMPLE 39

Effects of 1-(3'-pyridyl)-3-(2'-hydroxyethyl)thiourea hydrochloride on the cerebral carbohydrate and lactate metabolism, $Na^+$, $K^+$ - ATPase and water changes induced with triethyl tin sulfate.

Cerebral edema was induced in rats by a triethyl tin sulfate (5.0 mg/kg, i.p.) made on the whole brain. Edema was measured by the increase in water content, lactate, phosphorylase activity and the decrease in glycogen, $Na^+$, $K^+$ - ATPase activity of the whole brain.

1-(3'-Pyridyl)-3-(2'-hydroxyethyl)thiourea HCl was given 1 hour before and 24, 48 hours after the lesion treatment and the animals were killed by decapitation 72 hours after the lesion treatment.

When 1-(3'-pyridyl)-3-(2'-hydroxyethyl)thiourea HCl was given orally in the dosages of 100 and 300 mg/kg, the increase in lactate level and decrease in glycogen level and $Na^+$, $K^+$ - ATPase activity of the injured brain were antagonized. The results are shown in Table VI.

Table V

| Test compound | Dose (mg/kg, p.o.) | Number of rats | Phosphorylase (units/g) | | ATPase (μ moles Pi/g/hr) | $H_2O$ (%) | |
|---|---|---|---|---|---|---|---|
| | | | Active | A/T* × 100 | | Gray | White |
| Normal | — | 10 | 0.205 ± 0.005 | 64.1 ± 3.8 | 1.297 ± 0.062 | 80.9 | 79.6 |
| Control | — | 10 | 0.253 ± 0.007 | 79.6 ± 2.5 | 0.978 ± 0.035 | 82.6 | 80.1 |
| 1-(3'-Pyridyl)-3-(2'-hydroxyethyl)thiourea HCl | 100 | 5 | 0.242 ± 0.019 | 68.5 ± 2.5 | 1.180 ± 0.094 | 81.5 | 80.3 |
| | 300 | 5 | 0.220 ± 0.057 | 66.4 ± 2.7 | 1.226 ± 0.080 | 79.7 | 79.5 |

Note:
*A/T: Active phosphorylase/Total phosphorylase
**Pi: Inorganic phosphor

Table VI

| Test compound | Dose (mg/kg, p.o.) | Glycogen (mg/g) | Lactate (μg/g) | Phosphorylase (units/g) | | ATPase (μ moles Pi/g/hr)** | $H_2O$ (%) | |
|---|---|---|---|---|---|---|---|---|
| | | | | Active | A/T* × 100 | | Gray | White |
| Normal | — | 1.39 ±0.14 | 49.3 ± 2.8 | 0.170 ±0.009 | 63.2 ± 2.2 | 1.296 ±0.058 | 79.6 | 77.8 |
| | | 0.96 | 74.8 | 0.204 | 74.9 | 1.138 | | |

Table VI-continued

| Test compound | Dose (mg/kg, p.o.) | Glycogen (mg/g) | Lactate (µg/g) | Phosphorylase (units/g) Active | Phosphorylase (units/g) A/T* × 100 | ATPase (µ moles Pi/g/hr)** | H₂O (%) Gray | H₂O (%) White |
|---|---|---|---|---|---|---|---|---|
| Control | — | ±0.11 | ± 6.3 | ±0.013 | ± 4.0 | ±0.073 | 82.7 | 79.3 |
| 1-(3'-Pyridyl)- | | 1.03 | 72.5 | 0.197 | 73.3 | 1.146 | | |
| 3-(2'-hydroxy- | 30 | ±0.12 | ±5.2 | ±0.013 | ± 3.2 | ±0.062 | 81.6 | 79.5 |
| ethyl)thiourea | | 1.17 | 65.5 | 0.192 | 71.5 | 1.193 | | |
| HCl | 100 | ±0.09 | ± 3.8 | ±0.007 | ± 5.3 | ±0.077 | 80.2 | 78.3 |
| | | 1.27 | 61.0 | 0.187 | 67.8 | 1.246 | | |
| | 300 | ±0.11 | ± 4.2 | ±0.010 | ± 2.6 | ±0.051 | 79.4 | 77.8 |

Note:
*A/T: Active phosphorylase/Total phosphorylase
**Pi: Inorganic phosphor

EXAMPLE 40

Effects of 1-(3'-pyridyl)-3-(2'-hydroxyethyl)thiourea hydrochloride on the cardiac carbohydrate, lactate and fat under the influence of isoproterenol in an anoxic condition.

Male rats of wister - strain served as experimental animals. Isoproterenol in a dose of 3.0 µg/kg was injected intravenously to the animals, and 5 minutes later, the rat was taken to a closed room which was filled with a mixture gas consisting of 5 % oxygen and 95 % nitrogen. After the rat was kept in the above mentioned gas chamber for 5 minutes, they were killed by cervical dislocation. The anoxic state of the heart was measured by the cardiac carbohydrate (glycogen, pyruvate), lactate and fat [non-esterified fatty acid (hereinafter, referred to as NEFA), triglyceride (hereinafter, referred to as TG)].

In isoproterenol-treated rats under the anoxic condition, the decrease in cardiac glycogen content, the increase in pyruvate, lactate and NEFA levels were antagonized by 1-(3'-pyridyl)-3-(2'-hydroxyethyl)thiourea HCl at the dosage of 1.0 mg/kg i.v. This effect was significantly when 1-(3'-pyridyl)-3-(2'hydroxyethyl)thiourea HCl was administered 10 – 30 minutes before isoproterenol treatment. The results are shown in Table VII.

EXAMPLE 41

Effects of 1-(3'-pyridyl)-3-(2'-hydroxyethyl)thiourea hydrochloride on the distribution of $^{14}C$ - glucose(U) to brain.

$^{14}C$ - glucose(U) was given intravenously (1.0 µC/mouse), and the animals were killed by decapitation 10 minutes after $^{14}C$ - glucose administration. 1-(3'-Pyridyl)-3-(2'-hydroxyethyl)thiourea HCl was given orally 300 mg/kg before $^{14}C$ - glucose administration. 1-(3'-Pyridyl)-3-(2'-hydroxyethyl)thiourea HCl increased the distribution of $^{14}C$ - glucose to brain, when it was given 60 – 120 minutes before $^{14}C$ - glucose administration. The results are shown in Table VIII.

Table VIII

| Test compound | Time before $^{14}C$-glucose (min) | Brain (× 10³ dpm/g) | Plasma (× 10³ dpm/ml) | Brain/Plasma |
|---|---|---|---|---|
| Control | — | 74.55 ± 4.21 | 35.20 ± 4.12 | 2.12 ± 0.17 |
| 1-(3'-Pyridyl)-3-(2'-hydroxyethyl)thiourea HCl | 30 | 88.90 ± 12.69 | 35.22 ± 2.36 | 2.52 ± 0.59 |
| | 60 | 93.76 ± 5.33 | 37.88 ± 3.15 | 2.48 ± 0.44 |
| | 120 | 96.80 ± 6.80 | 35.93 ± 0.95 | 2.69 ± 0.15 |

EXAMPLE 42

Effects of 1-(3'-(pyridyl)-3-(2'-hydroxyethyl)thiourea hydrochloride on the haemodynamic action in anesthetized dogs.

To study of 1-(3'-pyridyl)-3-(2'-hydroxyethyl)thiourea HCl on the haemodynamic action, five dogs of either sex were used under sodium pentobarbital anesthesia (30 mg/kg i.v.), the common carotid artery blood flow and the femoral artery blood flow were measured by the electromagnetic flow meter and the systolic blood pressure in the femoral artery was recorded with the pressure transducer.

When 1-(3'-pyridyl)-3-(2'-hydroxyethyl)thiourea HCl was given intravenously in dosages of 3 – 30 mg/kg, blood pressure decreased slightly (8 – 14 %), Table VII

| Test compound | Time before iso. | Number of rats | Glycogen (mg/g) | Pyruvate (µg/g) | Lactate (µg/g) | NEFA (µM/g) | TG (mg/g) |
|---|---|---|---|---|---|---|---|
| Normal | | 10 | 7.02 ± 0.68 | 22.1 ± 2.03 | 86.4 ± 9.3 | 3.76 ± 0.32 | 1.72 ± 0.12 |
| Control | | 10 | 4.15 ± 0.35 | 50.5 ± 3.89 | 161.0 ± 12.4 | 5.21 ± 0.28 | 2.51 ± 0.27 |
| 1-(3'-Pyridyl)-3-(2'-hydroxyethyl)thiourea HCl | 5 | 5 | 5.68 ± 0.45 | 38.4 ± 2.42 | 123.2 ± 10.7 | 4.26 ± 0.35 | 2.15 ± 0.21 |
| | 10 | 5 | 6.05 ± 0.51 | 29.5 ± 3.15 | 95.1 ± 8.2 | 4.12 ± 0.29 | 1.98 ± 0.13 |
| | 30 | 5 | 6.97 ± 0.41 | 25.2 ± 2.07 | 92.5 ± 9.7 | 3.87 ± 0.32 | 1.87 ± 0.19 |
| | 60 | 5 | 5.92 ± 0.62 | 39.3 ± 2.76 | 140.6 ± 12.3 | 4.58 ± 0.36 | 2.25 ± 0.18 | carotid artery blood flow increased (6 – 24 %) and, at the same times, femoral artery blood flow also increased (4 – 18 %). The action of 1-(3'-pyridyl)-3-(2'-hydroxyethyl)thiourea HCl to the common carotid artery blood flow was significantly (12 – 39 %) when it was given intra-common carotid artery (0.1 – 1.0 mg/kg). But, these effects of 1-(3'-pyridyl)-3-(2'-hydroxyethyl)thiourea HCl were relatively weak in comparison with that of papaverine hydrochloride.

EXAMPLE 43

Acute toxicity

Acute toxicity of 1-(3'-pyridyl)-3-(2'-hydroxyethyl)thiourea hydrochloride was determined in dd-strain male mice. $LD_{50}$ were over 2,000 mg/kg p.o. and 1350 mg/kg s.c. and 640 mg/kg i.v. In dose of $LD_{50}$ or more, 1-(3'-pyridyl)-3-(2'-hydroxyethyl)thiourea HCl caused the acute lethal toxic symptoms of sedation and paralysis.

What is claimed is:
1. 1-(3'-Pyridyl)-3-(1',1'-dimethyl-2'hydroxyethyl)-thiourea or its pharmaceutically acceptable acid addition salt.
2. 1-(3'-Pyridyl)-3-(2'-hydroxypropyl)thiourea or its pharmaceutically acceptable acid addition salt.
3. 1-(3'-Pyridyl)-3-(3'-carboxypropyl)thiourea or its pharmaceutically acceptable acid addition salt.

* * * * *